(12) United States Patent
Schade et al.

(10) Patent No.: US 6,329,483 B1
(45) Date of Patent: Dec. 11, 2001

(54) COPOLYMERS OF CARBOXYLIC ACIDS AND QUATERNARY AMMONIUM COMPOUNDS AND THE USE THEREOF AS THICKENERS OF DISPERSANTS

(75) Inventors: Christian Schade, Ludwigshafen; Axel Sanner, Frankenthal; Hans-Ulrich Wekel, Ellerstadt; Franz Frosch, Bad Duerkheim; Horst Westenfelder, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/313,175
(22) PCT Filed: Apr. 20, 1993
(86) PCT No.: PCT/EP93/00952
§ 371 Date: Sep. 29, 1994
§ 102(e) Date: Sep. 29, 1994
(87) PCT Pub. No.: WO93/22358
PCT Pub. Date: Nov. 11, 1993

(30) Foreign Application Priority Data

Apr. 29, 1992 (DE) .................................................. 42 13 971

(51) Int. Cl.[7] .......................... C08F 222/04; C08F 226/00
(52) U.S. Cl. .......................... 526/263; 526/271; 526/287; 526/307; 526/318.4; 526/318.43
(58) Field of Search .................................. 526/263, 271, 526/287, 292.2, 296, 307, 318.4, 318.43

(56) References Cited

U.S. PATENT DOCUMENTS 3,174,874 3/1965 Fikentscher et al. .
4,463,080 * 7/1984 Snow ................. 525/326.8

FOREIGN PATENT DOCUMENTS

| 1 108 436 | 6/1961 | (DE) . |
|---|---|---|
| 328 725 | 8/1989 | (EP) . |
| 335 624 | 10/1989 | (EP) . |
| 435 066 | 7/1991 | (EP) . |

\* cited by examiner

Primary Examiner—Christopher Henderson
(74) Attorney, Agent, or Firm—Keil & Weinkauf

(57) ABSTRACT

A copolymer obtainable by free-radical polymerization of
A) 50–99.99% by weight of an olefinically unsaturated $C_3$–$C_5$ monocarboxylic acid, of an olefinically unsaturated $C_4$–$C_8$ dicarboxylic acid or the anhydride thereof or a mixture of such carboxylic acids or anhydrides with B) 0.01–50% by weight of an olefinically unsaturated quaternary ammonium compound of the formula I or II

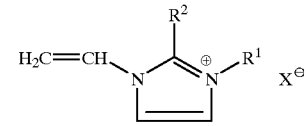

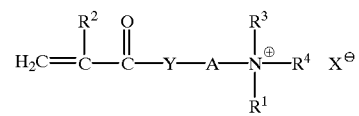

where
$R^1$ is $C_6$–$C_{20}$-alkyl, $C_6$–$C_{20}$-alkenyl, $C_5$–$C_8$-cycloalkyl, phenyl, phenyl($C_1$–$C_{12}$-alkyl) or ($C_1$–$C_{12}$-alkyl) phenyl,
$R^2$ is hydrogen, methyl or phenyl,
$R^3$ and $R^4$ are each H or $C_1$–$C_4$-alkyl,
X is halogen, $C_1$–$C_4$-alkoxysulfonyloxy or $C_1$–$C_4$-alkanesulfonate, it also being possible for the latter to occur as $R^3$ or $R^4$ with the formation of a betaine structure,
Y is O or NH, and
A is $C_1$–$C_6$-alkylene, or a mixture of such ammonium compounds, C) 0 to 49.99% by weight of an acrylate or methacrylate of the formula III

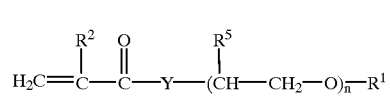

where $R^1$, $R^2$ and Y have the abovementioned meanings, $R^5$ is hydrogen, methyl or ethyl, and n is a number from 0 to 25, D) 0–49.99% by weight of other copolymerizable monomers and E) 0–5% by weight of one or more compounds with at least two olefinically unsaturated groups in the molecule as crosslinker. The copolymers are suitable as thickeners and dispersants, especially in cosmetic compositions.

4 Claims, No Drawings

COPOLYMERS OF CARBOXYLIC ACIDS AND QUATERNARY AMMONIUM COMPOUNDS AND THE USE THEREOF AS THICKENERS OF DISPERSANTS

BACKGROUND OF THE INVENTION

1. Field of the Invention

The present invention relates to novel copolymers of carboxylic acids and quaternary ammonium compounds, with or without acrylates or methacrylates, other copolymerizable monomers and crosslinkers. The present invention also relates to the use of these copolymers as thickeners or dispersants, in particular in cosmetic compositions, and to cosmetic compositions containing these copolymers.

2. Description of the Related Art

Thickeners or viscosity regulators conventionally used are copolymers of olefinically unsaturated carboxylic acids such as (meth)acrylic acid, maleic acid or maleic anhydride and hydrophobic comonomers such as esters of (meth)acrylic acid with or without small amounts of a crosslinker. Copolymers of this type are described, for example, in EP-A 328 725 (1) and EP-A 435 006 (2). Polymers of this type may occasionally be used as emulsifying components in water/oil mixtures. The polymers exert their thickening action once a considerable part of the acid functionality has been neutralized with a suitable base; they are then in the form of a polyanion.

Polymers of this type have some disadvantages. Since the hydrophobic comonomer is generally insoluble in water, the polymers must often be synthesized in an organic solvent. Solvents of this type are often a health hazard or even toxic. The content of hydrophobic comonomer makes these polymers generally dispersible in water only with difficulty. Furthermore, it is occasionally necessary to use very large amounts of the hydrophobic comonomer. Another disadvantage is that the stability to electrolytes is often low.

Polymers which have a large number of cationic groups are said likewise to be utilizable as thickeners or dispersants. Polymers of this type have a high affinity for the dispersed substances whose surfaces usually have a negative charge. Cationic polymers may therefore frequently have the opposite effect and lead to coalescence of existing dispersions; they are therefore also preferably used as flocculants.

DE-B 11 08 436 (3) describes copolymers of ethylenically unsaturated compounds which are sparingly soluble in water, eg. esters of unsaturated carboxylic acids, and N- or C-vinyl-substituted aromatic compounds which contain a quaternary N atom, eg. N-vinyl-N'-benzyl-imidazolium chloride. The substances are recommended for the finishing of textiles and for producing films and coatings.

SUMMARY OF THE INVENTION

It is an object of the present invention to provide novel polymers as thickeners and dispersants, specifically for cosmetic compositions, which no longer have the disadvantages of the prior art agents.

We have found that this object is achieved by a copolymer obtainable by free-radical polymerization of A) 50–99.99% by weight of an olefinically unsaturated $C_3$–$C_5$ monocarboxylic acid, of an olefinically unsaturated $C_4$–$C_8$ dicarboxylic acid or the anhydride thereof or a mixture of such carboxylic acids or anhydrides with B) 0.01–50% by weight of an olefinically unsaturated quaternary ammonium compound of the formula I or II

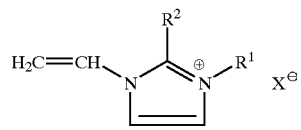

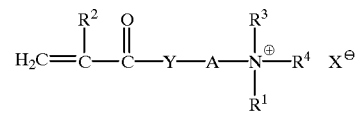

where $R^1$ is $C_6$–$C_{20}$-alkyl, $C_6$–$C_{20}$-alkenyl, $C_5$–$C_8$-cycloalkyl, phenyl, phenyl($C_1$–$C_{12}$-alkyl) or ($C_1$–$C_{12}$-alkyl) phenyl, $R^2$ is hydrogen, methyl or phenyl, $R^3$ and $R^4$ are each H or $C_1$–$C_4$-alkyl, X is halogen, $C_1$–$C_4$-alkoxysulfonyloxy or $C_1$–$C_4$-alkane-sulfonate, it also being possible for the latter to occur as $R^3$ or $R^4$ with the formation of a betaine structure, Y is O or NH, and A is $C_1$–$C_6$-alkylene, or a mixture of such ammonium compounds, C) 0 to 49.99% by weight of an acrylate or methacrylate of the formula III

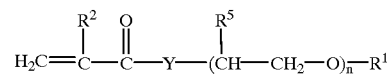

where $R^1$, $R^2$ and Y have the abovementioned meanings, $R^5$ is hydrogen, methyl or ethyl, and n is a number from 0 to 25, D) 0–49.99% by weight of other copolymerizable monomers and E) 0–5% by weight of one or more compounds with at least two olefinically unsaturated groups in the molecule as crosslinker.

DESCRIPTION OF THE PREFERRED EMBODIMENTS

In a preferred embodiment, the copolymer according to the invention is composed of A) 70–99.85% by weight of the carboxylic acid component A, B) 0.1–29.95% by weight of the quaternary ammonium compound I or II, C) 0–29.85% by weight of the acrylate or methacrylate III, D) 0–29.85% by weight of other copolymerizable monomers and E) 0.05–2% by weight of the crosslinker component E.

Particularly suitable as component A are acrylic acid, methacrylic acid and maleic anhydride, as well as crotonic acid, 2-pentenoic acid, maleic acid, fumaric acid or itaconic acid.

Suitable for $R^1$ in the quaternary ammonium compounds I or II of component B are $C_6$–$C_{20}$-alkyl, especially $C_{12}$–$C_{18}$-alkyl, eg. n-hexyl, n-octyl, 2-ethylhexyl, n-nonyl, isononyl, n-decyl, n-undecyl, n-dodecyl, n-tridecyl, isotridecyl, n-tetradecyl, n-pentadecyl, n-hexadecyl, n-heptadecyl, n-octadecyl or n-eicosyl, $C_6$–$C_{20}$-alkenyl, especially $C_{12}$–$C_{18}$-alkenyl, eg. oleyl, linolyl or linolenyl, $C_5$–$C_8$-cycloalkyl, eg. cyclopentyl, cyclohexyl, methylcyclohexyl or dimethylcyclohexyl, phenyl, phenyl($C_1$–$C_{12}$-alkyl), especially phenyl($C_1$–$C_4$-alkyl), eg. 2-phenylethyl, 3-phenylpropyl, 4-phenylbutyl or, in particular, benzyl, or ($C_1$–$C_{12}$-alkyl)phenyl, especially ($C_1$–$C_9$-alkyl)phenyl, eg. n-nonylphenyl, n-octylphenyl or o-, m- or p-tolyl.

$R^2$ in the compounds I or II is preferably hydrogen or methyl.

$R^3$ and $R^4$ in compound II are each preferably $C_1$–$C_3$-alkyl, ie. methyl, ethyl, n-propyl or isopropyl.

The anion X is halogen, especially chlorine or bromine, as well as iodine, $C_1$–$C_4$-alkoxysulfonyloxy, especially $C_1$–$C_3$-alkoxysulfonyloxy, in particular methoxysulfonyloxy or ethoxysulfonyloxy, $C_1$–$C_4$-alkanesulfonate, especially $C_1$–$C_3$-alkanesulfonate, in particular methanesulfonate or ethanesulfonate, or $C_1$–$C_4$-alkanesulfonate, in particular $C_1$–$C_3$-alkanesulfonate, which occurs as $R^3$ or $R^4$ with formation of a betaine structure, eg. 3-sulfopropyl.

The alkylene bridge A is preferably a straight-chain or branched $C_2$–$C_4$ bridge, eg. 1,2-ethylene, 1,3-propylene, 1,2-propylene, 2,3-butylene or 1,4-butylene, as well as pentamethylene or hexamethylene.

Quaternary ammonium compounds I or II which are very particularly preferred as component B are those where $R^1$ is $C_{12}$–$C_{18}$-alkyl, $C_{12}$–$C_{18}$-alkenyl, or benzyl, $R^2$ is hydrogen, methyl or phenyl, $R^3$ and $R^4$ are each $C_1$–$C_4$-alkyl, X is chlorine, bromine, methoxysulfonyloxy, ethoxysulfonyloxy, methanesulfonate, ethanesulfonate or $C_1$–$C_3$-alkanesulfonate, which occurs as $R^3$ or $R^4$ with formation of a betaine structure, Y is O or NH, and A is $C_2$–$C_4$-alkylene.

Particularly suitable as acrylates or methacrylates II for component C are stearyl acrylate, stearyl methacrylate, N-stearylacrylamide, N-stearylmethacrylamide, cetyl acrylate, cetyl methacrylate, lauryl acrylate, lauryl methacrylate, myristyl (meth)acrylate, behenyl acrylate, behenyl methacrylate or mixtures thereof. If the intention is to use (meth)acrylates or (meth)acrylamides III reacted with ethylene oxide, propylene oxide or butylene oxide, the degree of alkoxylation n is preferably from 3 to 25.

Examples of other copolymerizable monomers D which are suitable are N-vinylpyrrolidone, N-vinylcaprolactam, N-vinylimidazole, $C_1$–$C_6$-alkyl (meth)acrylates, eg. methyl (meth)acrylate or ethyl (meth)acrylate, or aminoalkyl (meth)acrylates or aminoalkyl (meth)acrylamides of the formula IV

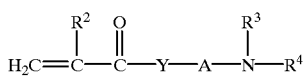

IV where $R^2$, $R^3$, $R^4$, Y and A have the abovementioned meanings.

The crosslinker component E is either a watersoluble compound such as divinylethyleneurea, bisacrylamidoacetic acid, methylenebisacrylamide, diallyltartaramide or (meth)acrylic esters of polyethylene glycols, for example tetraethylene glycol diacrylate or a water-insoluble compound such as ethylene glycol di(meth)acrylate, divinylbenzene, allyl methacrylate, trivinylcyclohexane, an aliphatic non-conjugated diene and, in particular, an allyl ether of trimethylolpropane, of pentaerythritol or of sucrose with at least two allyl ether units per molecule. Pentaerythritol triallyl ether, oleyl methacrylate, diallyltartaramide, bisacrylamidoacetic acid, methylenebisacrylamide or (meth)acrylic esters of polyethylene glycols are particularly preferred.

The preparation of the quaternary ammonium compounds I or II is known in principle or can be carried out in a similar way to known preparation methods. The preparation is carried out preferably by reacting an amine-functionalized (meth)acrylate or (meth)acrylamide and an N-vinylimidazole derivative, preferably N-vinylimidazole, with, for example, a long-chain alkyl halide at elevated temperature, if required in a suitable solvent which is, if required, removed after the reaction is complete, or in bulk. If required, the monomers B can be purified, for example, by reprecipitation or recrystallization from suitable solvent mixtures.

The appropriate organic halides, especially longchain alkyl chlorides, are reacted with N-vinylimidazole or with aminoalkyl (meth)acrylates or aminoalkyl (meth)acrylamides, preferably in polar solvents which are able to take on more than 0.5% by weight of water at room temperature. Examples of solvents of this type are alcohols, eg. ethanol, n-butanol, n-amyl alcohol or isopropanol, ketones such as acetone or methyl ethyl ketone, amides, eg. dimethylformamide, dimethylacetamide or N-methylpyrrolidone, nitriles such as acetonitrile, nitro compounds such as nitromethane or nitroethane, and glycol ethers, eg. ethylene glycol monomethyl ether or diethylene glycol dimethyl ether, sulfur compounds such as dimethyl sulfoxide or sulfolane, carbonates such as propylene carbonate or diethylene carbonate and esters such as ethyl acetate. Mixtures of these solvents can likewise be used. When the resulting products are soluble in the relevant media, it is also possible to use water or mixtures of water with the solvents described. Reaction temperatures above 40° C. are generally beneficial. To reach higher temperatures it is expedient in many cases to apply pressures up to 30 bar. The reaction can also be catalyzed by adding small amounts of an iodide or bromide.

The reaction can be carried out in the presence of approximately equimolar amounts of the alkylating agent. However, for the subsequent reaction to polymers it is often unnecessary to achieve complete alkylation. The reaction can therefore also be carried out in the presence of less than stoichiometric amounts of the alkylating agent. On the other hand, to achieve maximum degrees of alkylation, it is often expedient to carry out the reaction in the presence of an up to 4-fold excess of the alkylating agent. In this case, the excess alkylating agent is often removed from the product by a purification step.

The resulting compounds B or their solutions can advantageously be used directly for preparing the copolymers according to the invention. However, they can also be initially purified or isolated. To do this, the compounds can, for example, be recrystallized from a suitable solvent or precipitated with a precipitant. Examples of solvents of this type are acetone, ethyl acetate, tert-butyl methyl ether and hydrocarbons.

An advantageous way of preparing the copolymers according to the invention is precipitation polymerization in which the monomers are soluble, but the polymer is insoluble, in the solvent system used. Suitable solvents are aromatic compounds such as toluene, xylene or halogenated compounds such as 1,1,1-trichloroethane or methylene chloride, as well as semipolar solvents such as $C_3$–$C_6$ ketones or $C_1$–$C_6$-alkyl formates or acetates, also non-polar hydrocarbons, eg. cyclohexane or petroleum ether, and mixtures thereof. The polymer is obtained in the form of a fine-particle powder which is filtered off and dried in a suitable manner and, if required, finely ground.

Another polymerization technique is that of inverse emulsion or suspension polymerization. In contrast to alkyl (meth)acrylates or other lipophilic compounds, the cationic monomers B are at least partially soluble in water or mixtures of water with lower alcohols or ketones so that the polymerization can be carried out very advantageously in the hydrophilic phase of a water-in-oil emulsion. The oil phase is chosen to be a nonpolar liquid which is immiscible with water, such as a hydrocarbon, specifically liquid paraffin, or cyclohexane, as well as cosmetic oils. Protective colloids or emulsifiers are added to the system depending on required particle size of the product.

The free-radical polymerization is started by adding suitable initiators, for example alkali metal or ammonium persulfates, hydrogen peroxide or azo initiators or azo or oxo initiators which are soluble in the oil phase. Examples of the suitable initiator systems are diacyl peroxide such as dilauroyl peroxide, didecanoyl peroxide, dioctanoyl peroxide or dibenzoyl peroxide, peresters such as tert-butyl perneodecanoate, tert-butyl perethylhexanoate, t-butyl perpivalate, tert-amyl perneodecanoate, t-amyl perethylhexanoate or tert-butyl perisobutyrate or azo compounds such as 2,2'-azobis(2,4-dimethylvaleronitrile), 2,2'-azobisisobutyronitrile, dimethyl 2,2'-azobisisobutyrate or 2,2'-azobis(2-methylbutyronitrile).

The copolymers according to the invention are outstandingly suitable as thickeners or dispersants in industrial, pharmaceutical or, in particular, cosmetic compositions. They are able to form thickened gels and to stabilize emulsions permanently, as is required for cosmetic applications in, for example, creams, lotions or gels.

The copolymers according to the invention are generally very suitable for thickening aqueous systems such as suspensions of pigments in water, liquid detergents, aqueous polymer solutions and polymer dispersions. For this purpose, the polymer is adequately neutralized by adding a base such as triethanolamine, KOH, NaOH, 2-amino-2-methyl-1-propanol, 2-amino-2-methyl-1,3-propanediol, diisopropanolamine or tetrahydroxypropylethylenediamine. The polymers can be used in a similar way for preparing very stable thickened emulsions from a water phase and an oil phase. The amounts of the polymer used to obtained permanently stable emulsions are generally less than with conventional emulsifiers.

The present invention also relates to cosmetic compositions which contain the copolymers according to the invention as thickeners or dispersants in the amounts customary for this purpose, ie. about 0.05–2% by weight.

The copolymers according to the invention have a number of advantages:

The polymerization reaction for preparing them can, if required, be carried out in water because the cationic monomer B with a hydrophobic radical is at least partially soluble in water.

Particles in dispersed phases usually carry a negative charge (triboelectric effect). The cationic, amphiphilic groups in the polymer therefore have a good affinity for these phases. They are therefore able to form stable emulsions on use of smaller amounts.

The introduction of cationic groups into an anionic polymer in the thickening state confer partial ampholytic characteristics on the latter. This improves the electrolyte stability compared with conventional systems.

Cationic compounds have a high affinity for skin and hair. The emulsions prepared with the copolymers according to the invention are therefore particularly suitable for cosmetics intended for the skin and hair.

EXAMPLES

Unless otherwise indicated, percentages are by weight. Preparation of the Olefinically Unsaturated Quaternary Ammonium Compounds B

Examples 1 TO 3

N-Dodecyl-N'-vinylimidazolium bromide (Example 1)

98 g of N-vinylimidazole and 258 g of dodecyl bromide were dissolved in 500 ml of ethanol in a 2 l stirred vessel and stirred at 50° C. for 22 h. The crude product was concentrated, taken up again in acetone and precipitated by adding tert-butyl methyl ether. The isolated product was dried under reduced pressure. The following were prepared in a similar way:
Methacryloyloxy(dimethyl)dodecylammonium Chloride (Example 2) N-Dodecyl-N'-vinylimidazolium Chloride (Example 3)

Examples 4 TO 8

N-Hexadecyl-N'-vinylimidazolium bromide (Example 4)

15 g of N-vinylimidazole and 50 g of 1-bromohexadecane were stirred in a 500 ml vessel at 60° C. for 8 h. Then, 100 ml of ethyl acetate were added to this mixture while stirring. After a clear solution had formed, the heating and stirring was switched off. A colorless crystalline precipitate formed during the cooling to room temperature and was filtered off and dried.

The following were prepared in a similar way:
Methacryloyloxyethyl(dimethyl)hexadecylammonium bromide (Example 5)
N-Octadecyl-N'-vinylimidazolium chloride (Example 6)
N-Benzyl-N'-vinylimidazolium chloride (Example 7)
Methacrylamidopropyl(dimethyl)hexadecylammonium chloride (Example 8)
Preparation of the copolymers according to the invention

Examples 9 TO 26 (precipitation polymers)

1000 ml of solvent, 200 g of acrylic acid, the comonomers and pentaerythritol triallyl ether as cross-linker were stirred in a 3 l flanged flask and flushed with nitrogen for 30 min. The mixture was heated to 80° C. while stirring under a stream of nitrogen, and when this temperature was reached a mixture of 80 ml of solvent and 0.3 g of dilauroyl peroxide was added over the course of 3 h. After a further 4 h, the mixture was cooled, and the precipitate part was filtered off, washed with solvent and dried. The starting materials and the amounts thereof are indicated in Table 1.

TABLE 1

| | Composition of the precipitation polymers | | |
|---|---|---|---|
| Ex. No. | Comonomers (Component B from Ex. No.) | Pentaerythritol triallyl ether | Solvent (ratio by vol.) |
| 9 | 8.0 g 1 | 1.2 g | 1,1,1-trichloroethane |
| 10 | 8.0 g 2 | 1.2 g | 1,1,1-trichloroethane |
| 11 | 2.4 g 1<br>2.4 g stearyl methacrylate | 1.0 g | 1,1,1-trichloroethane |
| 12 | 4.0 g 4 | 1.2 g | 1,1,1-trichloroethane |
| 13 | 8.0 g 4 | 1.2 g | acetone |

TABLE 1-continued

Composition of the precipitation polymers

| Ex. No. | Comonomers (Component B from Ex. No.) | Pentaerythritol triallyl ether | Solvent (ratio by vol.) |
|---|---|---|---|
| 14 | 8.0 g 4 | 1.2 g | isopropyl acetate |
| 15 | 5.0 g 6 | 1.2 g | ethyl acetate/cyclohexane (1:1) |
| 16 | 5.0 g 7 | 1.2 g | 1,1,1-trichloroethane |
| 17 | 5.0 g 4 | 1.2 g | ethyl acetate/cyclohexane (1:1) |
| 18 | 2.5 g 4<br>2.5 g stearyl methacrylate | 0.8 g | ethyl acetate/cyclohexane (1:1) |
| 19 | 5.0 g 6 | 1.2 g | ethyl acetate/cyclohexane (1:1) |
| 20 | 10.0 g 6 | 1.2 g | cyclohexane |
| 21 | 1.0 g 4<br>5.0 g stearyl methacrylate | 1.2 g | cyclohexane |
| 22 | 10.0 g 5 | 1.2 g | isobutyl acetate |
| 23 | 5.0 g 8 | 1.2 g | ethyl acetate/cyclohexane (1:1) |
| 24 | 10.0 g 8 | 1.2 g | ethyl acetate/cyclohexane (1:3) |
| 25 | 4.0 g 4 | 0.6 g | 1,1,1-trichloroethane |
| 26 | 4.0 g 4 | 0.3 g | 1,1,1-trichloroethane |

Comparative Example A

The reaction was carried out as in Examples 9 to 26 with 5.0 g of stearyl methacrylate as sole comonomer and 1.2 g of pentaerythritol triallyl ether in 1,1,1-trichloroethane.

Comparative example B

The reaction was carried out as in Examples 9 to 26 with 10.0 g of stearyl methacrylate as sole comonomer and 1.2 g of pentaerythritol triallyl ether in a mixture of ethyl acetate and cyclohexane in the ratio 1:1 by volume.

Examples 27 TO 36
(Suspension polymers)

1000 ml of cyclohexane and a protective colloid or emulsifier were introduced into a 3 l flanged flask. After nitrogen had been passed in for 30 min, a mixture of 100 g water, 100 g of acrylic acid, 1 g of potassium peroxodisulfate and comonomers and, where appropriate, crosslinker was added dropwise while stirring at 75° C. over the course of 30 min. After a further 3 h, the mixture was heated to boiling, and the water was removed by azeotropic distillation. The remaining suspension of the polymer was filtered off, washed with cyclohexane and then dried under reduced pressure. The starting materials and their amounts are indicated in Table 2.

TABLE 2

Composition of the suspension polymers

| Ex. No. | Comonomers (Component B from Ex. No.) | Crosslinker | Protective colloid/ emulsifier |
|---|---|---|---|
| 27 | 4.0 g 1 | — | 2 g SMC |
| 28 | 4.0 g 1 | 0.8 g diallyl-tartaramide | 3 g SMC |
| 29 | 33.0 g SPMAEDMA<br>5.3 g 1 | — | 2 g SMC |
| 30 | 4.0 g 1 | — | 2 g Dowfax 2A1 |

TABLE 2-continued

Composition of the suspension polymers

| Ex. No. | Comonomers (Component B from Ex. No.) | Crosslinker | Protective colloid/ emulsifier |
|---|---|---|---|
| 31 | 2.0 g 1 | — | 3 g Dowfax 2A1 |
| 32 | 4.0 g 6 | 0.1 g bisacryl-amidoacetic acid | 2 g Dowfax 2A1 |
| 33 | 2.0 g 4 | 0.1 g polyethyleneglycol 200 bis-acrylate | 4 g of a technical stearyl alcohol with degree of ethoxylation n = 7 |
| 34 | 2.0 g 6 | — | 4 g Dowfax 2A1 |
| 35 | 4.0 g 4 | — | 2 g Dowfax 2A1 |
| 36 | 2.0 g 4 | 0.1 g methylene-bisacrylamide | 2 g polyvinyl-pyrrolidone |

SMC=styrene/maleic acid copolymer (90:10)
SPMAEDMA=3-sulfopropylmethacryloyloxyethyldimethylammonium betaine
Dowfax 2A1=sodium salt of a disulfonic acid of an alkylated diphenyl ether.

Use properties

PREPARATION OF GELS 1.0 g of one of the polymers from Examples 9 to 36 and Comparative Examples A and B was dispersed in 190 ml of water in a beaker. While stirring, 10 ml of a 10% strength triethanolamine solution were added.

The viscosity of the resulting gels was determined using a manual viscometer (Haake VT-02) (see Table 3 for results). The gels were then spread on a glass plate to check the smooth texture by inspection.

The gels were made up as stated in water and in 1% strength NaCl solution. Comparison of viscosities of the two gels demonstrates the greater salt stability of the partially ampholytic polymers according to the invention (see Tab. 4 for results).

PREPARATION OF EMULSIONS 0.4 g of polymer was weighed into a beaker and dispersed in 30 ml of liquid paraffin. Then 100 ml of water and subsequently 4 ml of a 10% strength triethanolamine solution were added while stirring vigorously. The emulsion was then homogenized with a disperser at 8000 rpm for a few s. The viscosity was determined as above (see Table 3 for results). The long-term stability was checked by examining the emulsion for any phase separation after standing in a 100 ml cylinder for 14 d.

TABLE 3

Viscosities of gels and emulsions

| Example No. | Gel viscosity [Pas] | Emulsion viscosity [Pas] |
|---|---|---|
| Comp. Ex. A | 12 | 9 |
| Comp. Ex. B | 5 | 4.3 |
| 9 | 8.5 | 6.2 |
| 10 | 4.5 | 6.4 |
| 11 | 13 | 13.9 |
| 12 | 20 | 19.8 |
| 13 | 16 | 10.2 |

TABLE 3-continued

Viscosities of gels and emulsions

| Example No. | Gel viscosity [Pas] | Emulsion viscosity [Pas] |
| --- | --- | --- |
| 14 | 9.2 | 7.8 |
| 15 | 10.1 | 8.8 |
| 16 | - lump formation - | — |
| 17 | 18.0 | 11.1 |
| 18 | 6.3 | 3.9 |
| 19 | 7.5 | 11.0 |
| 20 | 4.1 | 6.4 |
| 21 | 12.5 | 11.7 |
| 22 | 14 | 12 |
| 23 | 9.2 | 13 |
| 24 | 12.1 | 9.6 |
| 25 | 15.2 | 14.1 |
| 26 | 10.8 | 10 |
| 27 | 4.1 | 3.8[a] |
| 28 | - lump formation - | — |
| 29 | 3.9 | 4.8 |
| 30 | 5.2 | 4.7[a] |
| 31 | 3.9 | 4.6 |
| 32 | 11.2 | 9.6 |
| 33 | 8.4 | 6.6 |
| 34 | 4.6 | 5.3 |
| 35 | 7.6 | 8.1 |
| 36 | 10.4 | 12 |

[a] slight oil separation after 14 h

TABLE 4

Comparison of the viscosities of the gels in water and in NaCl solution

| Example No. | Viscosity in water/viscosity in 1% strength NaCl solution |
| --- | --- |
| Comp. Ex. A | 200 |
| Comp. Ex. B | 180 |
| 10 | 30 |
| 11 | 70 |
| 15 | 45 |
| 20 | 25 |
| 23 | 40 |
| 25 | 60 |
| 29 | 50 |

The dispersibility of the polymers was checked by spreading the emulsion from Table 3 on a glass plate with a flat spatula and inspecting the thin film under a microscope. The following average particle sizes were found:
Comparative Example A 30 μm
Example 10 8.5 μm
Example 13 20 μm
Example 18 15 μm
Example 19 6 μm The smaller particle size of the emulsions obtained with the polymers according to the invention was an indicator of the improved emulsion stability of these phases.

We claim:

1. A copolymer obtainable by free-radical polymerization of

A) 50–99.99% by weight of an olefinically unsaturated $C_3$–$C_5$ monocarboxylic acid, of an olefinically unsaturated $C_4$–$C_8$ dicarboxylic acid or the anhydride thereof or a mixture of such carboxylic acids or anhydrides with B) 0.1–29.95% by weight of an olefinically unsaturated quaternary ammonium compound of the formula I or II

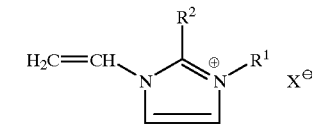

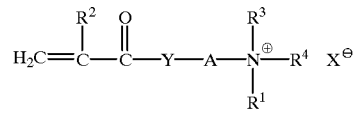

where $R^1$ is $C_6$–$C_{20}$-alkyl, $C_6$–$C_{20}$-alkenyl, $C_5$–$C_8$-cycloalkyl, phenyl, phenyl($C_1$–$C_{12}$-alkyl) or ($C_1$–$C_{12}$-alkyl) phenyl, $R^2$ is hydrogen, methyl or phenyl, $R^3$ and $R^4$ are each H or $C_1$–$C_4$-alkyl, X is halogen, $C_1$–$C_4$-alkoxysulfonyloxy or $C_1$–$C_4$-alkanesulfonate, it also being possible for the latter to occur as $R^3$ or $R^4$ with the formation of a betaine structure, Y is O or NH, and A is $C_1$–$C_6$-alkylene, or a mixture of such ammonium compounds, C) 0 to 49.99% by weight of an acrylate or methacrylate of the formula III

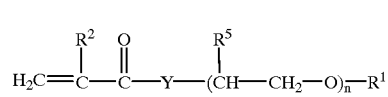

where $R^1$, $R^2$ and Y have the abovementioned meanings, $R^5$ is hydrogen, methyl or ethyl, and n is a number from 0 to 25, D) 0–29.85% by weight of other copolymerizable monomers and E) 0.5–2% by weight of one or more compounds with at least two olefinically unsaturated groups in the molecule as crosslinker.

2. A copolymer as defined in claim 1, in whose preparation acrylic acid, methacrylic acid or maleic anhydride has been used as component A.

3. A copolymer as defined in claim 1, in whose preparation quaternary ammonium compounds I or II where $R^1$ is $C_{12}$–$C_{18}$-alkyl, $C_{12}$–$C_{18}$-alkenyl, or benzyl, $R^2$ is hydrogen, methyl or phenyl, $R^3$ and $R^4$ are each $C_1$–$C_4$-alkyl, X is chlorine, bromine, methoxysulfonyloxy, ethoxysulfonyloxy, methanesulfonate or ethanesulfonate, Y is O or NH, and A is $C_2$–$C_4$-alkylene, have been used as component B.

4. A copolymer as defined in claim 1, in whose preparation pentaerythritol triallyl ether, oleyl methacrylate, diallyltartaramide, bisacrylamidoacetic acid, methylenebisacrylamide or a polyethylene glycol di(meth)acrylate has been used as component E.

* * * * *

UNITED STATES PATENT AND TRADEMARK OFFICE
CERTIFICATE OF CORRECTION

PATENT NO. : 6,329,483 B1
DATED : December 11, 2001
INVENTOR(S) : Schade et al.

It is certified that error appears in the above-identified patent and that said Letters Patent is hereby corrected as shown below:

Column 9,
Line 58, "obtainable" should be -- obtained --.
Line 60, "50-99.99" should be -- 70-99.85 --.

Signed and Sealed this

Twentieth Day of August, 2002

Attest:

JAMES E. ROGAN
Attesting Officer  Director of the United States Patent and Trademark Office